US007156810B2

(12) United States Patent  
Cho et al.

(10) Patent No.: US 7,156,810 B2
(45) Date of Patent: Jan. 2, 2007

(54) BLOOD SUGAR LEVEL MEASURING METHOD AND APPARATUS

(75) Inventors: Ok-Kyung Cho, Schwerte (DE); Yoon-Ok Kim, Schwerte (DE)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/781,675

(22) Filed: Feb. 20, 2004

(65) Prior Publication Data

US 2005/0080324 A1 Apr. 14, 2005

(30) Foreign Application Priority Data

Oct. 8, 2003 (JP) ............................. 2003-349792

(51) Int. Cl.
A61B 5/05 (2006.01)
(52) U.S. Cl. ..................................... 600/365
(58) Field of Classification Search ........ 600/300–301, 600/306, 309–313, 316–324, 326, 549, 345–348, 600/347–365

See application file for complete search history.

(56) References Cited

U.S. PATENT DOCUMENTS

| | | | |
|---|---|---|---|
| 4,306,569 A | 12/1981 | Weil | |
| 4,333,803 A | 6/1982 | Seger | |
| 4,509,531 A * | 4/1985 | Ward | 600/549 |
| 4,750,140 A | 6/1988 | Asano | |
| 4,802,489 A | 2/1989 | Nitzan | |
| 5,551,422 A | 9/1996 | Simonsen | |
| 5,676,143 A | 10/1997 | Simonsen | |
| 5,725,480 A | 3/1998 | Oosta et al. | |
| 5,732,711 A | 3/1998 | Fitzpatrick | |
| 5,743,262 A | 4/1998 | Lepper, Jr. | |
| 5,769,784 A | 6/1998 | Barnett | |
| 5,795,305 A | 8/1998 | Cho et al. | 600/549 |
| 5,857,966 A * | 1/1999 | Clawson | 600/300 |
| 5,899,855 A * | 5/1999 | Brown | 600/301 |
| 5,924,996 A * | 7/1999 | Cho et al. | 600/549 |
| 6,226,089 B1 | 5/2001 | Hakamata | |
| 6,240,306 B1 | 5/2001 | Rohrscheib | |
| 6,269,314 B1 * | 7/2001 | Iitawaki et al. | 702/23 |
| 6,280,381 B1 | 8/2001 | Malin | |
| 6,322,504 B1 * | 11/2001 | Kirshner | 600/300 |
| 6,353,226 B1 | 3/2002 | Khalil | |
| 6,615,061 B1 | 9/2003 | Khalil | |
| 2002/0183646 A1 | 12/2002 | Stivoric et al. | |
| 2003/0152133 A1 | 8/2003 | Ellenz | |

(Continued)

FOREIGN PATENT DOCUMENTS

EP 0 778 000 A1 6/1997

(Continued)

OTHER PUBLICATIONS

R.M. Hillson, et al., "Facial and Sublingual Temperature Changes Following Intravenous Glucose Injection In Diabetics", Diabete & Metabolisme (Paris) 1982, vol. 8, pp. 15-19.

(Continued)

Primary Examiner—Robert L. Nasser
Assistant Examiner—Patricia Mallari
(74) Attorney, Agent, or Firm—Antonelli, Terry, Stout and Kraus, LLP

(57) ABSTRACT

Blood sugar levels are measured in a non-invasive way based on temperature measurement. Different regression functions are used for an able-bodied person and a diabetic patient when stabilizing measurement data by correcting a non-invasively measured blood sugar level, i.e. a value obtained by temperature measurement, with blood oxygen saturation and blood flow volume.

11 Claims, 11 Drawing Sheets

U.S. PATENT DOCUMENTS

2004/0225209 A1* 11/2004 Cho et al. .................. 600/365

FOREIGN PATENT DOCUMENTS

| JP | 06 317566 | 11/1994 |
| --- | --- | --- |
| JP | 7-71945 | 3/1995 |
| JP | 08 322821 | 12/1996 |
| JP | 10-33512 | 2/1998 |
| JP | 10-108857 | 4/1998 |
| JP | 11 505451 | 5/1999 |
| JP | 11 155840 | 6/1999 |
| JP | 11-230901 | 8/1999 |
| JP | 11 318872 | 11/1999 |
| JP | 2000 074829 | 3/2000 |
| JP | 2000 506048 | 5/2000 |
| JP | 2000-258343 | 9/2000 |
| JP | 2002 535023 | 10/2002 |
| JP | 2003 510556 | 3/2003 |
| WO | WO 01/28414 | 4/2001 |
| WO | WO 03/010510 | 2/2003 |

OTHER PUBLICATIONS

A.R. Scott, et al., "Diabetes Mellitus and Thermoregulation", Can. J. Physiol, Pharmacol, vol. 65, 1987, pp. 1365-1376.
European Search Report 04001496.1-1526 dated Dec. 29, 2004.
European Search Report 04003188.2-1526 dated Jan. 26, 2005.
XP002313054, Database accession No. PREV198682093889, Database Biosis Online, Biosciences Information Service, Kanluan et al., Comparison of Plasma and Whole Blood Glucose Determination.

* cited by examiner

BLOOD SUGAR LEVEL MEASURING METHOD AND APPARATUS

BACKGROUND OF THE INVENTION

1. Field of the Invention

The present invention relates to non-invasive measurement of blood sugar levels for measuring glucose concentration in a living body without blood sampling.

2. Background Art

Hilson et al. report facial and sublingual temperature changes in diabetics following intravenous glucose injection (Non-Patent Document 1). Scott et al. discuss the issue of diabetics and thermoregulation (Non-Patent Document 2). Based on the knowledge gained from such researches, Cho et al. suggest a method and apparatus for determining blood glucose concentration by temperature measurement without requiring the collection of a blood sample (Patent Documents 1 and 2).

Various other attempts have been made to determine glucose concentration without blood sampling. For example, a method has been suggested (Patent Document 3) whereby a measurement site is irradiated with near-infrared light of three wavelengths, and the intensity of transmitted light as well as the temperature of the living body is detected. A representative value of the second-order differentiated value of absorbance is then calculated, and the representative value is corrected in accordance with the difference of the living body temperature from a predetermined reference temperature. The blood sugar level corresponding to the thus corrected representative value is then determined. An apparatus is also provided (Patent Document 4) whereby a measurement site is heated or cooled while monitoring the living body temperature. The degree of attenuation of light based on light irradiation is measured at the moment of temperature change so that the glucose concentration responsible for the temperature-dependency of the degree of light attenuation can be measured. Further, an apparatus is reported (Patent Document 5) whereby an output ratio between reference light and the light transmitted by an irradiated sample is taken, and then the glucose concentration is calculated from a linear expression of the logarithm of the output ratio and the living body temperature. Another method has been reported (Patent Document 6) whereby the contribution of skin parameter such as melanin or the thickness of skin is measured to correct the non-invasive measurement of glucose concentration, for example.

(Non-Patent Document 1) R. M. Hilson and T. D. R. Hockaday, "Facial and sublingual temperature changes following intravenous glucose injection in diabetics," Diabete & Metabolisme, 8, pp.15–19: 1982

(Non-Patent Document 2) A. R. Scott, T. Bennett, I. A. MacDonald, "Diabetes mellitus and thermoregulation," Can. J. Physiol. Pharmacol., 65, pp. 1365–1376: 1987

(Patent Document 1) U.S. Pat. No. 5,924,996

(Patent Document 2) U.S. Pat. No. 5,795,305

(Patent Document 3) JP Patent Publication (Kokai) No. 2000-258343 A (Patent Document 4) JP Patent Publication (Kokai) No. 10-33512 A (1998)

(Patent Document 5) JP Patent Publication (Kokai) No. 10-108857 A (1998)

(Patent Document 6) U.S. Pat. No. 5,725,480

SUMMARY OF THE INVENTION

Glucose (blood sugar) in blood is used for glucose oxidation reaction in cells to produce necessary energy for the maintenance of living bodies. In the basal metabolism state, in particular, most of the produced energy is converted into heat energy for the maintenance of body temperature. Thus, it can be expected that there is some relationship between blood glucose concentration and body temperature. However, as is evident from the way sicknesses cause fever, the body temperature also fluctuates due to factors other than blood glucose concentration. While methods have been proposed to determine blood glucose concentration by temperature measurement without blood sampling, they lack sufficient accuracy.

It is the object of the invention to provide a method and apparatus for determining blood glucose concentration with high accuracy based on temperature data of the test subject without blood sampling.

Blood sugar is delivered to the cells throughout the human body via blood vessel systems, particularly the capillary blood vessels. In the human body, complex metabolic pathways exist. Glucose oxidation is a reaction in which, fundamentally, blood sugar reacts with oxygen to produce water, carbon dioxide, and energy. Oxygen herein refers to the oxygen delivered to the cells via blood. The volume of oxygen supply is determined by the blood hemoglobin concentration, the hemoglobin oxygen saturation, and the volume of blood flow. On the other hand, the heat produced in the body by glucose oxidation is dissipated from the body by convection, heat radiation, conduction, and so on. It is said that an able-bodied person has a better glucose oxidation efficiency than a diabetic patient. Thus, it can be thought that in the state of high sugar levels, in particular, an able-bodied person produces more amount of heat than a diabetic patient when they have the same level of blood glucose concentration. On the assumption that the body temperature is determined by the balance between the amount of energy produced in the body by glucose burning, namely heat production, and heat dissipation such as mentioned above, the inventors set up the following model:

(1) The amount of heat production and the amount of heat dissipation are considered equal.
(2) The amount of heat production is a function of the blood glucose concentration and the volume of oxygen supply.
(3) The volume of oxygen supply is determined by the blood hemoglobin concentration, the blood hemoglobin oxygen saturation, and the volume of blood flow in the capillary blood vessels.
(4) The amount of heat dissipation is mainly determined by heat convection and heat radiation.
(5) The relationship between the blood glucose level and the amount heat produced varies between diabetic patient and able-bodied person.

According to this model, we achieved the present invention after realizing that blood sugar levels can be accurately determined on the basis of the results of measuring the temperature of the body surface and simultaneously measuring parameters relating to the blood oxygen concentration and to the blood flow volume. The parameters can be measured, e.g., from a part of the human body, such as the fingertip. The parameters relating to convection and radiation can be determined by carrying out thermal measurements on the fingertip. The parameters relating to the blood hemoglobin concentration and the blood hemoglobin oxygen saturation can be determined by spectroscopically measuring blood hemoglobin and then finding the ratio between hemoglobin bound with oxygen and hemoglobin not bound with oxygen. The parameter relating to the volume of blood flow can be determined by measuring the amount of heat transfer from the skin.

The invention provides a blood sugar level measuring apparatus comprising: a measuring portion for obtaining a plurality of measurement values related to a body surface and a measurement environment; a selecting means for selecting an able-bodied person or a diabetic patient; and calculation portion for calculating a blood sugar level based on the plurality of measurement values obtained in the measuring portion and the result of selection by the selecting means. The blood sugar level measuring apparatus further comprises a storage portion in which a plurality of regression functions are stored. The calculation portion reads a regression function corresponding to the result of selection from the storage portion to calculate a blood sugar level. More specifically, the storage portion stores a plurality of regression functions and a mean value and a standard deviation of, a plurality of parameters corresponding to individual regression functions. The calculation portion reads a regression function corresponding to the result of selection, the mean value of the parameters and the standard deviation from the storage portion and then calculates a blood sugar level.

The invention further provides a blood sugar level measuring apparatus comprising: an input means for entering an input identifying an able-bodied person or a diabetic patient; a heat amount measuring portion for measuring a plurality of temperatures derived from a body surface in order to obtain information used for calculating the amount of transfer of heat by convection and the amount of transfer of heat by radiation, which relate to the dissipation of heat from the body surface; an oxygen amount measuring portion for obtaining information relating to the amount of oxygen in blood; a storage portion in which a function for able-bodied persons and a function for diabetic patients are individually stored, the functions relating parameters corresponding to the plurality of temperatures and the blood oxygen amount to blood sugar levels; a calculation portion for converting a plurality of measurement values inputted from the heat amount measuring portion and the oxygen amount measuring portion into the parameters individually, and applying the parameters to the function stored in the storage portion for the able-bodied persons or for the diabetic patients, depending on the identifying input entered via the input means, in order to calculate a blood sugar level; and a display portion for displaying the blood sugar level calculated by the calculation portion. The storage portion stores a regression function for able-bodied persons and another regression function for diabetic patients, and the calculation portion calculates a blood sugar level using the regression function corresponding to the identifying input. More specifically, the storage portion stores a regression function for able-bodied persons, a regression function for diabetic patients, and a mean value and standard deviation of a plurality of parameters included in each regression function. The calculation portion calculates a blood sugar level using a regression function corresponding to the identifying input and a mean value and standard deviation associated with that regression function. The oxygen amount measuring portion comprises a blood flow volume measuring portion for obtaining information relating to the volume of blood flow, and an optical measuring portion for obtaining the hemoglobin concentration and hemoglobin oxygen saturation in blood.

The invention provides a blood sugar level measuring method comprising the steps of: obtaining a plurality of measurement values relating to a body surface and a measurement environment; obtaining the type identifying an able-bodied person or a diabetic patient; and calculating a blood sugar level using the obtained plurality of measurement values and a regression function for either able-bodied persons or diabetic patients. The step of calculating blood sugar level comprises: obtaining a plurality of parameters from the obtained plurality of measurement values; normalizing the obtained plurality of parameters with a mean value and standard deviation corresponding to the type, i.e. whether an able-bodied person or a diabetic patient; and calculating a blood sugar level by applying the normalized plurality of parameters to the regression function corresponding to the able-bodied person or the diabetic patient.

In accordance with the invention, a highly accurate non-invasive blood sugar level measuring apparatus and method can be provided.

DESCRIPTION OF THE PREFERRED EMBODIMENTS

The invention will now be described by way of preferred embodiments thereof with reference made to the drawings.

Initially, the aforementioned model will be described in more specific terms. The model will be described in specific terms for a diabetic patient and an able-bodied person individually in view of item (5) of the model.

Regarding the amount of heat dissipation, convective heat transfer, which is one of the main causes of heat dissipation, is related to temperature difference between the ambient (room) temperature and the body-surface temperature.

Another main cause of dissipation, namely the amount of heat dissipation due to radiation, is proportional to the fourth power of the body-surface temperature according to the Stefan-Boltzmann law. Thus, it can be seen that the amount of heat dissipation from the human body is related to the room temperature and the body-surface temperature. On the other hand, the oxygen supply, which is another major factor related to the amount of heat production, is expressed as the product of hemoglobin concentration, hemoglobin oxygen saturation, and blood flow volume.

The hemoglobin concentration can be measured from the absorbance at the wavelength (equal-absorbance wavelength) at which the molar absorbance coefficient of the oxyhemoglobin is equal to that of the deoxyhemoglobin. The hemoglobin oxygen saturation can be measured by measuring the absorbance at the equal-absorbance wavelength and the absorbance at at least one different wavelength at which the ratio between the molar absorbance coefficient of the oxyhemoglobin and that of the deoxyhemoglobin is known, and then solving simultaneous equations. Namely, the hemoglobin concentration and hemoglobin oxygen saturation can be obtained by conducting the measurement of absorbance at at least two wavelengths.

The rest is the blood flow volume, which can be measured by various methods. One example will be described below.

Figure 1:
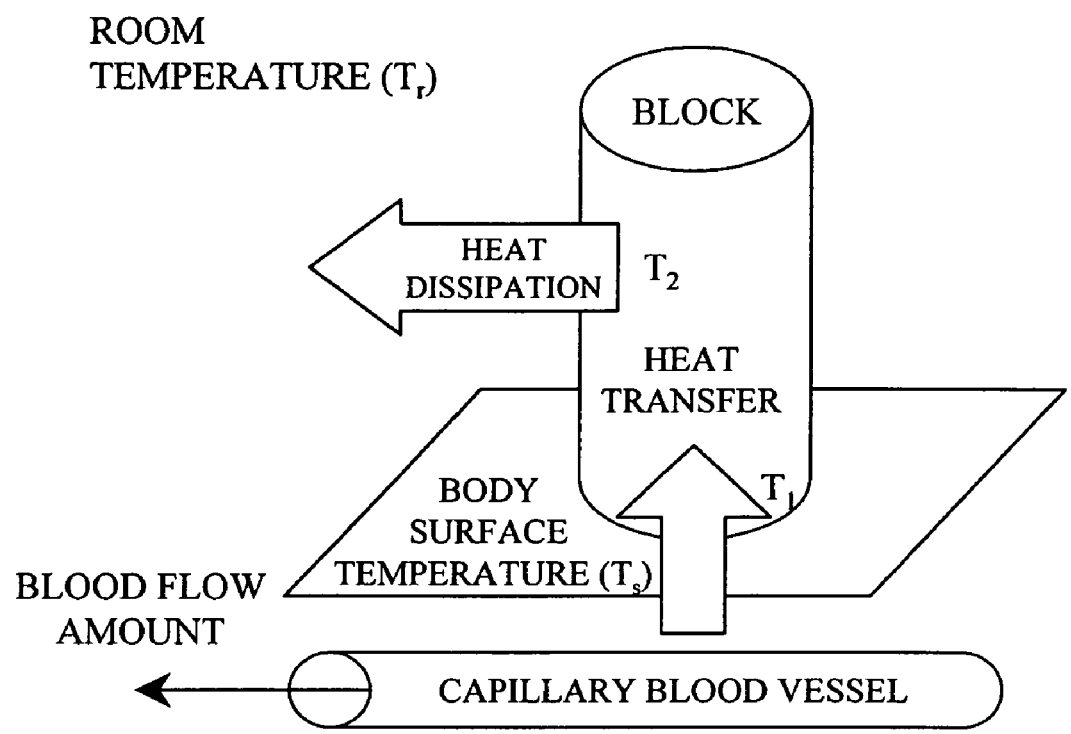
FIG. 1 shows a model of heat transfer from the body surface to a block.

FIG. 1 shows a model of the transfer of heat from the body surface to a solid block having a certain heat capacity when the block is brought into contact with the body surface for a certain time and then separated. The block is made of resin such as plastic or vinyl chloride. In the illustrated example, attention will be focused on the chronological variation of the temperature $T_1$ of a portion of the block that is brought into contact with the body surface, and the chronological variation of the temperature $T_2$ of a point on the block away from the body surface. The blood flow volume can be estimated by monitoring mainly the chronological variation of the temperature $T_2$ (of the spatially separated point on the block). The details will follow.

Before the block comes into contact with the body surface, the temperatures $T_1$ and $T_2$ at the two points of the block are equal to the room temperature $T_r$. When a body-surface temperature $T_s$ is higher than the room temperature $T_r$, the temperature $T_1$ swiftly rises due to the transfer of heat from the skin as the block comes into contact with the body surface, and it approaches the body-surface temperature $T_s$. On the other hand, the temperature $T_2$ is lower than the temperature $T_1$ as the heat conducted through the block is dissipated from the block surface, and it rises more gradually than the temperature $T_1$. The chronological variation of the temperatures $T_1$ and $T_2$ depends on the amount of heat transferred from the body surface to the block, which in turn depends on the blood flow volume in the capillary blood vessels under the skin. If the capillary blood vessels are regarded as a heat exchanger, the coefficient of transfer of heat from the capillary blood vessels to the surrounding cell tissues is given as a function of the blood flow volume. Thus, by measuring the amount of heat transfer from the body surface to the block by monitoring the chronological variation of the temperatures $T_1$ and $T_2$, the amount of heat transferred from the capillary blood vessels to the cell tissues can be estimated. Based on this estimation, the blood flow volume can then be estimated. Thus, by measuring the amount of heat transfer from the body surface to the block by monitoring the temperature variation of the $T_1$ and $T_2$ in time, the amount of heat transferred from the capillary blood vessels to the cell tissues can be estimated.

Figure 2:
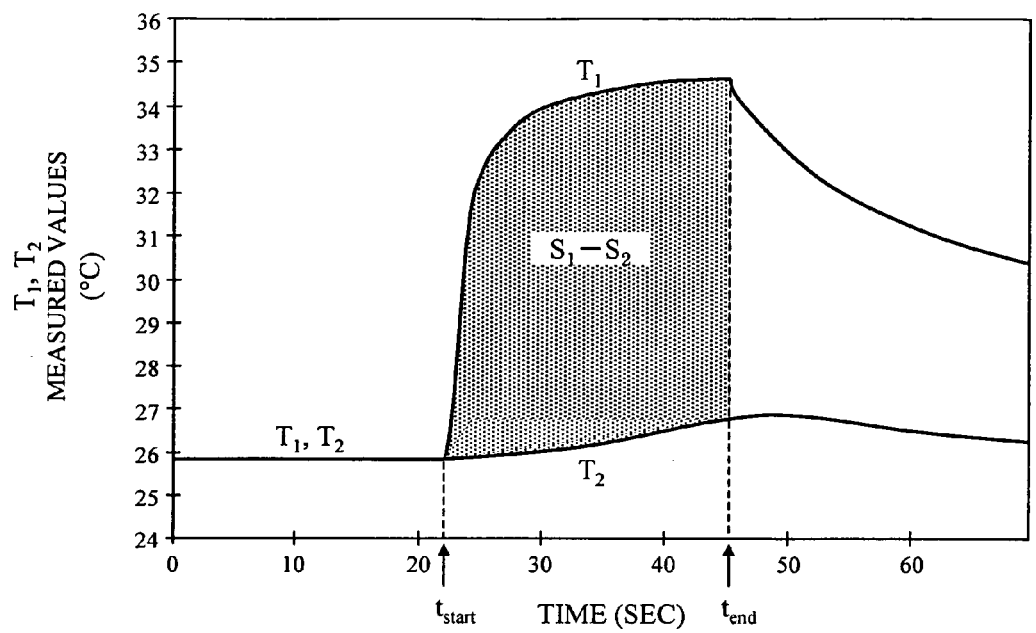
FIG. 2 plots the measurement values of temperatures $T_1$ and $T_2$ as they change with time.

FIG. 2 shows the chronological variation of the measured values of the temperature $T_1$ at the portion of the block that is in contact with the body surface and the temperature $T_2$ at the position on the block away from the body-surface contact position. As the block comes into contact with the body surface, the $T_1$ measured value swiftly rises, and it gradually drops as the block is brought out of contact.

Figure 3:
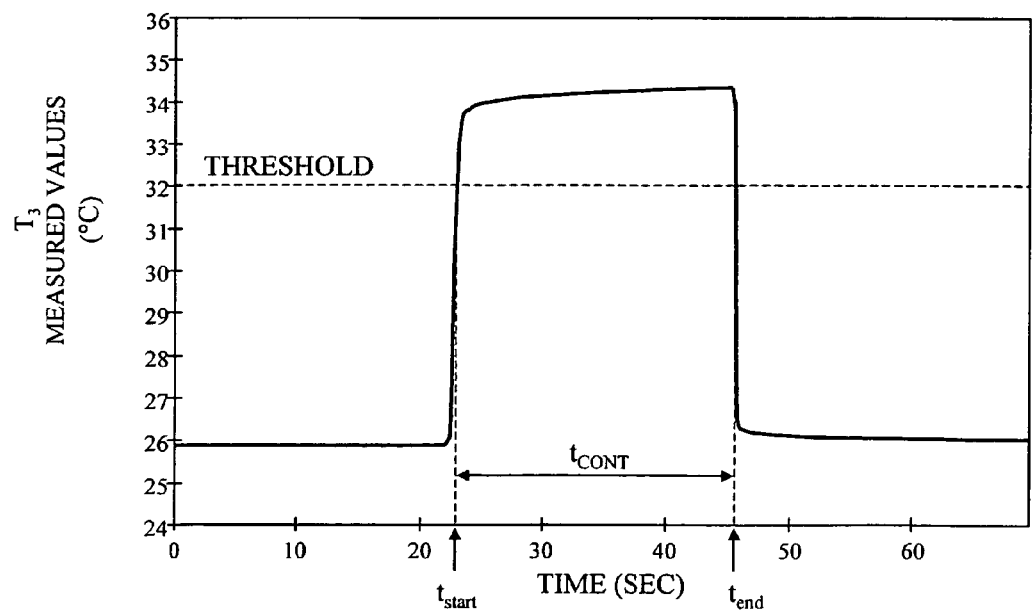
FIG. 3 shows an example of measuring the chronological change in temperature $T_3$.
Figure 7:
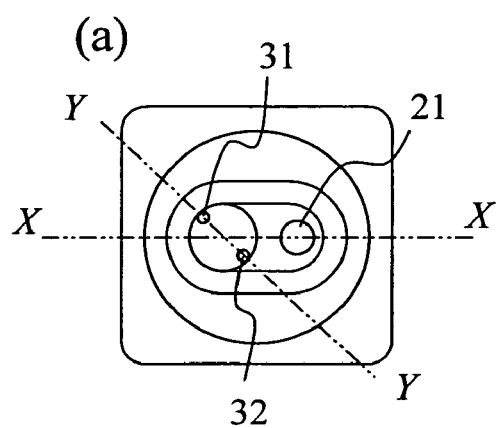
FIG. 7 shows the measuring portion in detail.
Figure 7:
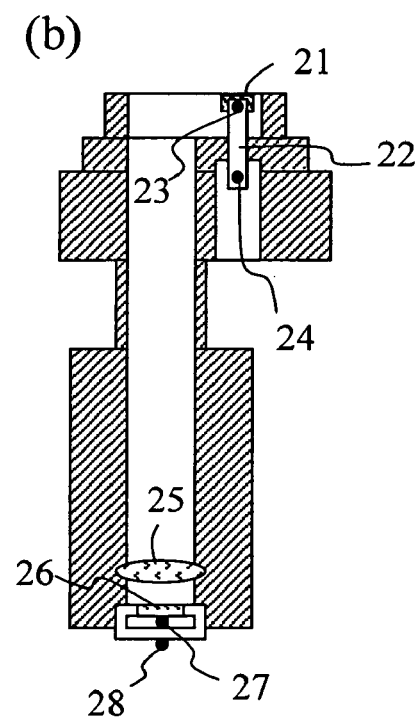
Figure 7:
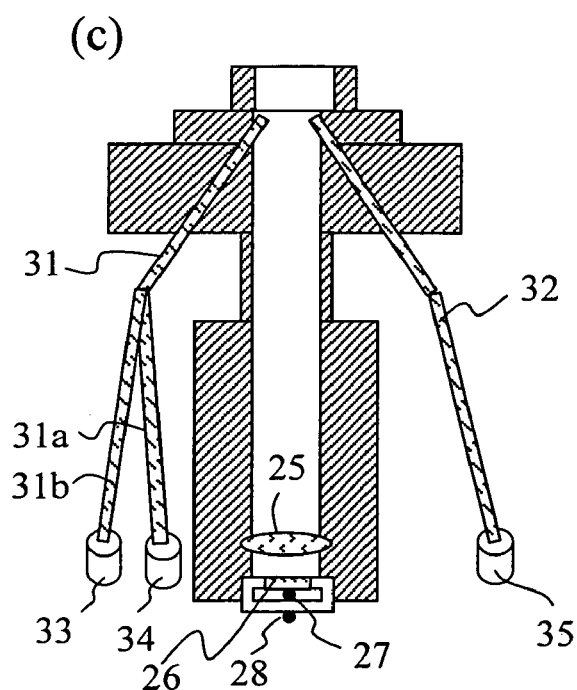

FIG. 3 shows the chronological variation of the value of the temperature $T_3$ measured by a radiation temperature detector. As the detector detects the temperature due to radiation from the body surface, it is more sensitive to temperature changes than other sensors. Because radiation heat propagates as an electromagnetic wave, it can transmit temperature changes instantaneously. Thus, by locating the radiation temperature detector near where the block contacts the body surface to measure the heat radiated from the body surface, as shown in FIG. 7 (which will be described later), the time of start of contact $t_{start}$ and the time of end of contact $t_{end}$ between the block and the body surface can be detected from changes in the temperature $T_3$. For example, a temperature threshold value is set as shown in FIG. 3. The contact start time $t_{start}$ is when the temperature threshold value is exceeded. The contact end time $t_{end}$ is when the temperature $T_3$ drops below the threshold. The temperature threshold is set at 32° C., for example.

Then, the $T_1$ measured value between $t_{start}$ and $t_{end}$ is approximated by an S curve, such as a logistic curve. A logistic curve is expressed by the following equation:

$$T = \frac{b}{1 + c \times \exp(-a \times t)} + d$$

where T is temperature, and t is time.

The measured value can be approximated by determining coefficients a, b, c, and d by the non-linear least-squares method. For the resultant approximate expression, T is integrated between time $t_{start}$ and time $t_{end}$ to obtain a value $S_1$.

Similarly, an integrated value $S_2$ is calculated from the $T_2$ measured value. The smaller $(S_1-S_2)$ is, the larger the amount of transfer of heat from the body surface to the position of $T_2$. $(S_1-S_2)$ becomes larger with increasing body-surface contact time $t_{cont}$ (=$t_{end}-t_{start}$). Thus, $a_5/(t_{cont} \times (S_1-S_2))$ is designated as a parameter $X_5$ indicating the volume of blood flow, using $a_5$ as a proportionality coefficient.

Thus, it will be seen that the measured amounts necessary for the determination of blood glucose concentration by the above-described model are the room temperature (ambient temperature), body surface temperature, temperature changes in the block brought into contact with the body surface, the temperature due to radiation from the body surface, and the absorbance at at least two wavelengths.

Figure 4:
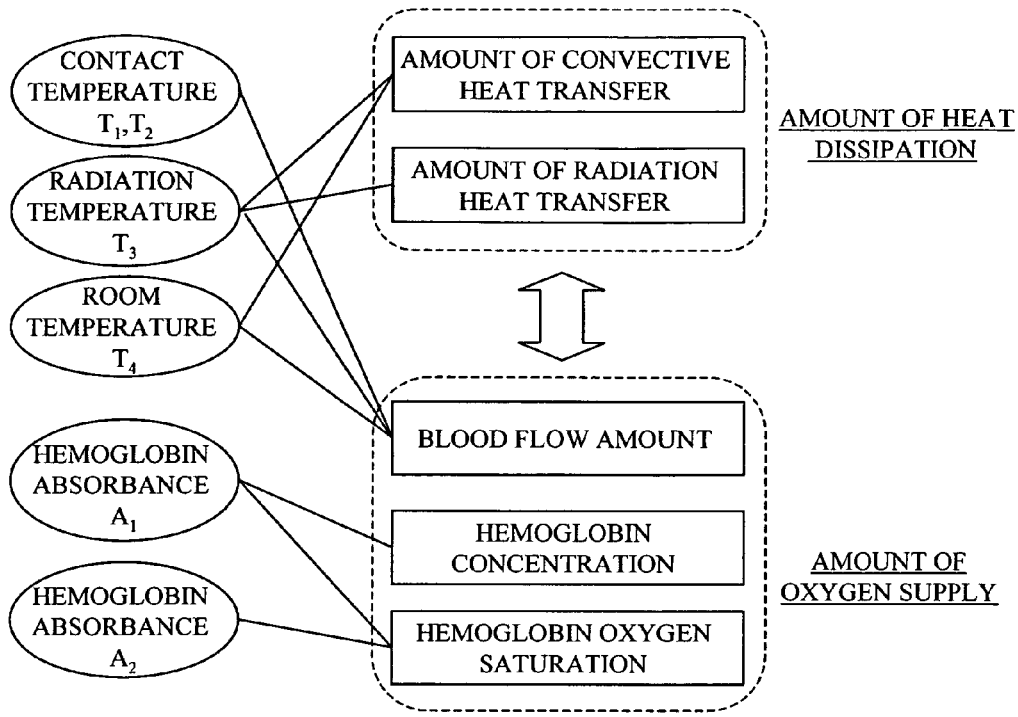
FIG. 4 shows the relationships between measurement values provided by various sensors and the parameters derived therefrom.

FIG. 4 shows the relationships between the measured values provided by various sensors and the parameters derived therefrom. A block is brought into contact with the body surface, and chronological changes in two kinds of temperatures $T_1$ and $T_2$ are measured by two temperature sensors provided at two locations of the block. Separately, radiation temperature $T_3$ on the body surface and room temperature $T_4$ are measured. Absorbance $A_1$ and $A_2$ are measured at at least two wavelengths related to the absorption of hemoglobin. The temperatures $T_1$, $T_2$, $T_3$, and $T_4$ provide parameters related to the volume of blood flow. The temperature $T_3$ provides a parameter related to the amount of heat transferred by radiation. The temperatures $T_3$ and $T_4$ provide parameters related to the amount of heat transferred by convection. The absorbance $A_1$ provides a parameter relating to the hemoglobin concentration, and the absorbance $A_1$ and $A_2$ provide parameters relating to the hemoglobin oxygen saturation. Hereafter, an apparatus for non-invasively measuring blood sugar levels according to the principle of the invention will be described.

Figure 5:
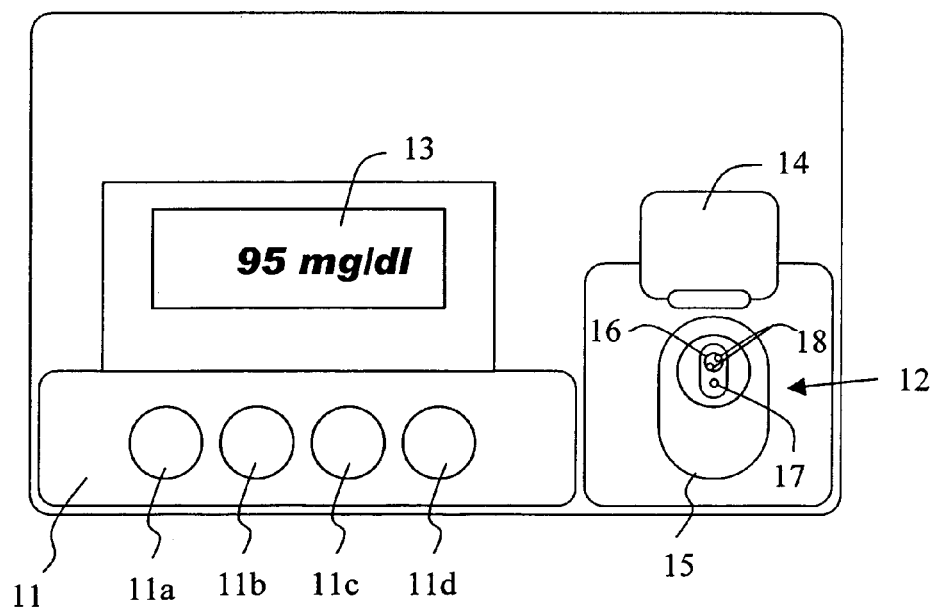
FIG. 5 shows an upper plan view of a non-invasive blood sugar level measuring apparatus according to the present invention.

FIG. 5 shows a top plan view of a non-invasive blood sugar level measuring apparatus according to the invention. While in this example the skin on the ball of the finger tip is used as the body surface, other parts of the body surface may be used.

On the top surface of the apparatus are provided an operating portion 11, a measuring portion 12 where the finger to be measured is to be placed, and a display portion 13 for displaying measurement results, the state of the apparatus, and measured values, for example. The operating portion 11 includes four push buttons 11a to 11d for operating the apparatus. The measuring portion 12 has a cover 14 which, when opened (as shown), reveals a finger rest portion 15 with an oval periphery. The finger rest portion 15 accommodates an opening end 16 of a radiation temperature sensor portion, a contact temperature sensor portion 17, and an optical sensor portion 18.

Figure 6:
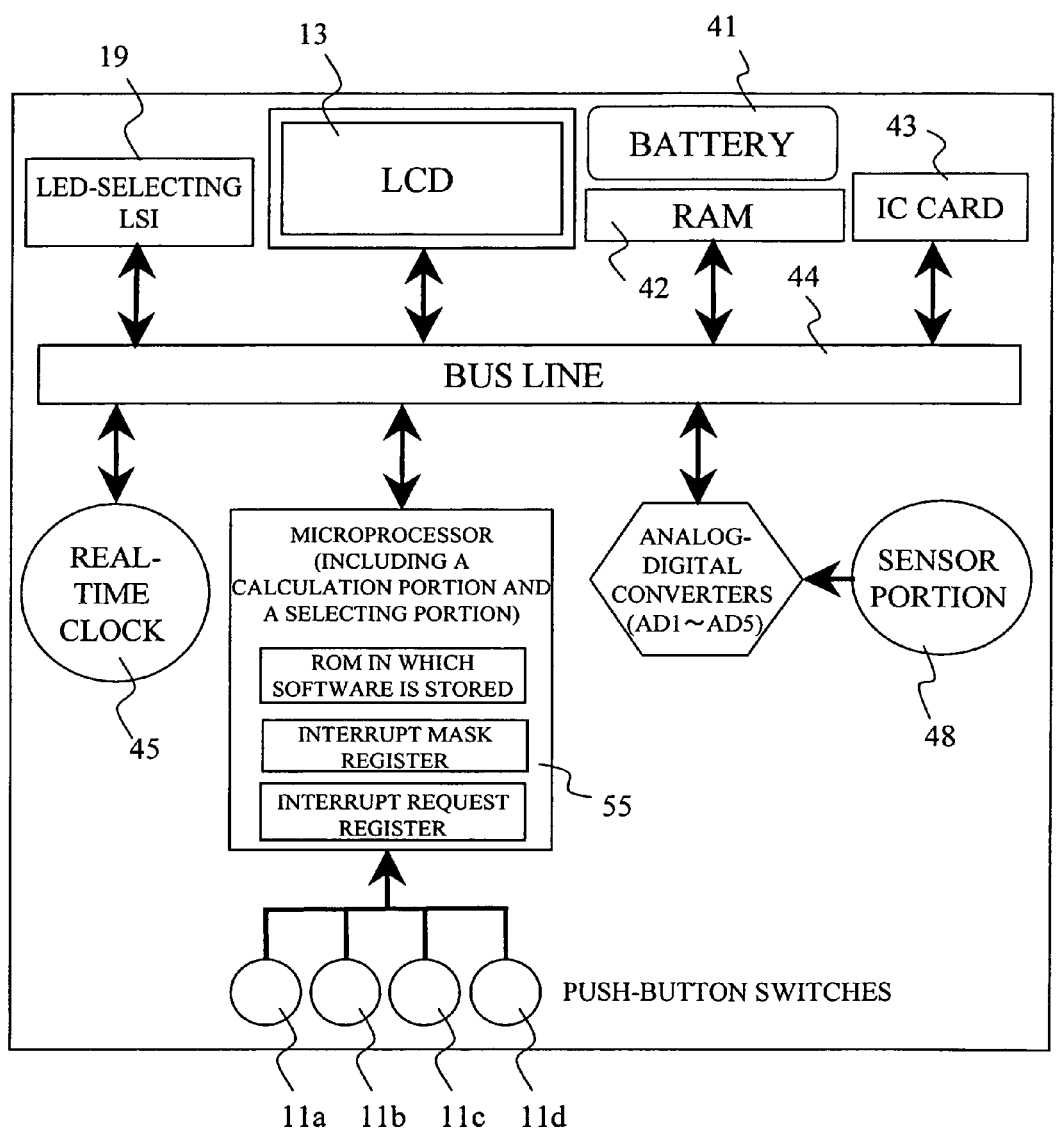
FIG. 6 shows a functional block diagram of the apparatus.

FIG. 6 shows a functional block diagram of the apparatus. The present apparatus is driven by a battery 41. Signals obtained by a sensor portion comprising a temperature sensor and an optical sensor are supplied to analog/digital converters AD1 to AD5 for individual signals, where they are converted into digital signals. An LED selecting LSI 19 is controlled by a microprocessor 55 such that two light-emitting diodes as the light sources of the optical sensor can emit light in a time-sharing manner. The microprocessor 55 includes peripheral circuits such as the analog-digital converters AD1 to AD5, LCD 13, LED-selecting LSI 19, RAM 42, IC card 43 and a real-time clock 45. These peripheral circuits can be accessed individually by the microprocessor 55 via a bus line 44. Push buttons 11a to 11d are connected to the microprocessor 55.

The microprocessor 55 has a ROM for the storage of software. The microprocessor further includes an interrupt request register and an interrupt mask register as registers relating to interrupt processing requests that are entered by the pressing of the buttons 11a to 11d. The interrupt request register is a register for identifying the button that has been pressed when entering a an interrupt processing request to the microprocessor. The interrupt mask register is made up of one bit. By setting the mask register to 1 using software, the mask register can prevent the reception of, i.e. masking, the interrupt processing request via the pressing of the push button. When the register is set to 0 using software, the masking of the interrupt processing request can be removed. Thus, the software controls the various registers, accesses information stored in ROM and selects particular information stored therein according to a request entered via the buttons, and perform calculations using the ROM-stored information, for example. The microprocessor also includes a selecting portion and a calculating portion, as will be described later.

FIG. 7 shows the measuring portion in detail. In FIG. 7, (a) is a top plan view, (b) is a cross section taken along line X—X of (a), and (c) is a cross section taken along line Y—Y of (a).

First, the process of measuring temperatures by the non-invasive blood sugar level measuring apparatus according to the invention will be described. In the portion of the measuring portion where the examined portion (ball of the finger) is to come into contact, a thin plate 21 of a highly heat-conductive material, such as gold, is placed. A bar-shaped heat-conductive member 22 made of material such as polyvinylchloride whose heat conductivity is lower than that of the plate 21 is thermally connected to the plate 21 and extends into the apparatus. The temperature sensors include a thermistor 23 for measuring the temperature of the plate 21 by acting as an adjacent-temperature detector with respect to the examined portion. There is also a thermistor 24 for measuring the temperature of a portion of the heat-conducting member which is distanced away from the plate 21 by a certain distance and acting as an indirect-temperature detector with respect to the examined portion. An infrared lens 25 is disposed inside the apparatus at such a position that the examined portion (ball of the finger) placed on the finger rest portion 15 can be seen through the lens. Below the infrared lens 25 is disposed a thermopile 27 via an infrared radiation-transmitting window 26. Another thermistor 28 is disposed near the thermopile 27.

Thus, the temperature sensor portion of the measuring portion includes four temperature sensors, which measure four kinds of temperatures as follows:

(1) Temperature on the finger surface (thermistor 23): $T_1$
(2) Temperature of the heat-conducting member (thermistor 24): $T_2$
(3) Temperature of radiation from the finger (thermopile 27): $T_3$
(4) Room temperature (thermistor 28): $T_4$ The optical sensor unit 18 measures the hemoglobin concentration and the hemoglobin oxygen saturation necessary for the determination of the oxygen supply volume. In order to measure the hemoglobin concentration and the hemoglobin oxygen saturation, absorption must be measured at at least two wavelengths. FIG. 7(c) shows a configuration for carrying out the two-wavelength measurement using two light sources 33 and 34 and one detector 35.

Inside the optical sensor unit 18 are disposed the ends of two optical fibers 31 and 32. The optical fiber 31 is for optical irradiation, and the optical fiber 32 is for receiving light. As shown in FIG. 7(c), the optical fiber 31 connects to branch fibers 31a and 31b that are provided with light-emitting diodes 33 and 34 at the respective ends thereof. The other end of the light-receiving optical fiber 32 is provided with a photodiode 35. The light-emitting diode 33 emits light with a wavelength of 810 nm, while the light-emitting diode 34 emits light with a wavelength of 950 nm. The wavelength 810 nm is the equal absorption wavelength at which the molar absorbance coefficient of the oxy-hemoglobin is equal to that of the deoxy-hemoglobin. The wavelength 950 nm is the wavelength at which the difference between the molar absorbance coefficient of the oxy-hemoglobin and that of the deoxy-hemoglobin is large.

The two light-emitting diodes 33 and 34 emit light in a time-sharing manner such that the finger of the subject is irradiated with the light emitted by the light-emitting diodes 33 and 34 via the irradiating optical fiber 31. The light shone on the finger is reflected by the skin, enters the light-receiving optical fiber 32, and is eventually detected by the photodiode 35. The light shone on the finger is reflected by the skin of the finger, but part of the light penetrates the skin and enters into the tissues and is then absorbed by the hemoglobin in the blood flowing in the capillary blood vessels. The measurement data provided by the photodiode 35 has reflectance R, and the absorbance can be approximately calculated by $\log(1/R)$. The finger is thus irradiated with light with the wavelengths of 810 nm and 950 nm, and R is measured for each and also log(1/R) is calculated for each. Thus, absorption $A_1$ and $A_2$ for wavelengths 810 nm and 950 nm, respectively, are measured.

When the deoxy-hemoglobin concentration is [Hb] and the oxy-hemoglobin concentration is [HbO$_2$], absorption $A_1$ and $A_2$ are expressed by the following equations:

$$A_1 = a \times ([\text{Hb}] \times A_{Hb}(810 \text{ nm}) + [\text{HbO}_2] \times A_{HbO_2}(810 \text{ nm}))$$

$$= a \times ([\text{Hb}] + [\text{HbO}_2]) \times A_{HbO_2}(810 \text{ nm})$$

$$A_2 = a \times ([\text{Hb}] \times A_{Hb}(950 \text{ nm}) + [\text{HbO}_2] \times A_{HbO_2}(950 \text{ nm}))$$

$$= a \times ([\text{Hb}] + [\text{HbO}_2]) \times \left(\left(1 - \frac{[\text{HbO}_2]}{[\text{Hb}] + [\text{HbO}_2]}\right) \times A_{Hb}(950 \text{ nm}) + \frac{[\text{HbO}_2]}{[\text{Hb}] + [\text{HbO}_2]} \times A_{HbO_2}(950 \text{ nm})\right)$$

$A_{Hb}(810 \text{ nm})$ and $A_{Hb}(950 \text{ nm})$, and $A_{HbO2}(810 \text{ nm})$ and $A_{HbO2}(950 \text{ nm})$ are the molar absorbance coefficients of the deoxy-hemoglobin and the oxy-hemoglobin, respectively, and are known at the respective wavelengths. The term a is a proportionality coefficient. The hemoglobin concentration [Hb]+[HbO$_2$], and the hemoglobin oxygen saturation [HbO$_2$]/([Hb]+[HbO$_2$]) can be determined from the above equations as follows:

$$[\text{Hb}] + [\text{HbO}_2] = \frac{A_1}{a \times A_{HbO_2}(810 \text{ nm})}$$

$$\frac{[\text{HbO}_2]}{[\text{Hb}] + [\text{HbO}_2]} = \frac{A_2 \times A_{HbO_2}(810 \text{ nm}) - A_1 \times A_{Hb}(950 \text{ nm})}{A_1 \times (A_{HbO_2}(950 \text{ nm}) - A_{Hb}(950 \text{ nm}))}$$

In the present example, the hemoglobin concentration and the hemoglobin oxygen saturation are measured by measuring absorbance at two wavelengths. Preferably, however, absorbance may be measured at more than two wavelengths so that the influence of interfering components can be reduced and measurement accuracy can be improved.

Figure 8:
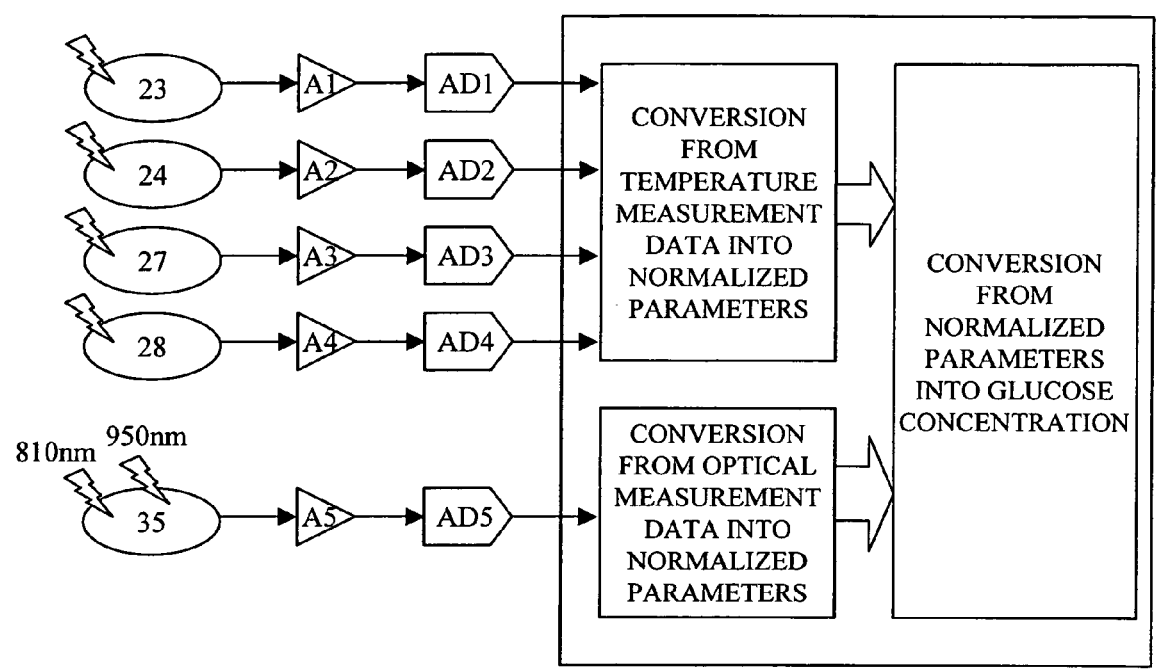
FIG. 8 shows a concept chart illustrating the flow of processing of data in the apparatus.

FIG. 8 shows the concept of how data is processed in the apparatus. The apparatus according to the present example is equipped with five sensors, namely thermistor 23, thermistor 24, pyroelectric detector 27, thermistor 28, and photodiode 35. The photodiode 35 measures absorption at wavelengths 810 nm and 950 nm. Thus, the apparatus is supplied with six kinds of measurement values.

The five kinds of analog signals are supplied via individual amplifiers A1 to A5 to analog/digital converters AD1 to AD5, where they are converted into digital signals. Based on the digitally converted values, parameters $x_i$ (i=1, 2, 3, 4, 5) are calculated. The following are specific descriptions of $x_i$ (where $a_1$ to $a_5$ are proportionality coefficients):

Parameter proportional to heat radiation $$x_1 = a_1 \times (T_3)^4$$

Parameter proportional to heat convection $$x_2 = a_2 \times (T_1 - T_3)$$

Parameter proportional to hemoglobin concentration $$x_3 = a_3 \times \left(\frac{A_1}{a \times A_{HbO_2}(810 \text{ nm})}\right)$$

Parameter proportional to hemoglobin saturation $$x_4 = a_4 \times \left(\frac{A_2 \times A_{HbO_2}(810 \text{ nm}) - A_1 \times A_{Hb}(950 \text{ nm})}{A_1 \times (A_{HbO_2}(950 \text{ nm}) - A_{Hb}(950 \text{ nm}))}\right)$$

Parameter proportional to blood flow volume $$x_5 = a_5 \times \left(\frac{1}{t_{CONT} \times (S_1 - S_2)}\right)$$

Then, normalized parameters are calculated from mean values and standard deviations of parameters $x_i$. A normalized parameter $X_i$ (where i=1, 2, 3, 4, 5) is calculated from each parameter $x_i$ according to the following equation:

$$X_i = \frac{x_i - \bar{x}_i}{SD(x_i)}$$

where $x_i$: parameter $\bar{x}_i$: mean value of the parameter $SD(x_i)$: standard deviation of the parameter Using the above five normalized parameters, calculations are conducted for conversion into glucose concentration to be eventually displayed. A program necessary for the processing calculations is stored in a ROM in the microprocessor built inside the apparatus. The memory region required for the processing calculations is ensured in a RAM similarly built inside the apparatus. The results of calculation are displayed on the LCD display.

The ROM stores, as a constituent element of the program necessary for the processing calculations, a regression function for determining glucose concentration C in particular. The regression function is determined in advance for the diabetic patient and the able-bodied person individually. Specifically, it is determined by the least-squares method using the glucose concentration measured from many diabetic patients and able-bodied persons using the enzymatic electrode method, which is an invasive method, and the normalized parameters that were simultaneously obtained for the many diabetic patients and able-bodied persons. When a common regression function is used that has been determined from a measured data group in which diabetic patients and able-bodied persons exist together, it can be thought that the correlation coefficient with the glucose concentration obtained by the enzymatic electrode method, in light of item (5) of the aforementioned model that says "The relationship between the blood glucose level and the amount heat produced varies between diabetic patient and able-bodied person." Thus, a regression function is determined for the diabetic patients and the able-bodied persons individually from a data group of diabetic patients and a data group of able-bodied persons, and the individual regression functions are stored in the ROM.

The function is defined as follows, in which a regression function for the diabetic patients will be used as an example. C is expressed by the below-indicated equation (1), where $a_{Di}$ (i=0, 1, 2, 3, 4, 5) is determined from measurement data obtained from a number of diabetic patients in advance according to the following procedure:

(1) A multiple regression equation is created that indicates the relationship between the normalized parameter and the glucose concentration C.
(2) A normalized equation (simultaneous equations) relating to the normalized parameter is obtained from an equation obtained by the least-squares method.
(3) Values of coefficient $a_{Di}$ (i=0, 1, 2, 3, 4, 5) are determined from the normalized equation and then substituted into the multiple regression equation.

Initially, a regression equation (1) indicating the relationship between the glucose concentration C and normalized parameters $X_{D1}$, $X_{D2}$, $X_{D3}$, $X_{D4}$, and $X_{D5}$ is formulated.

$$C = f(X_{D1}, X_{D2}, X_{D3}, X_{D4}, X_{D5}) \qquad (1)$$
$$= a_{D0} + a_{D1}X_{D1} + a_{D2}X_{D2} + a_{D3}X_{D3} + a_{D4}X_{D4} + a_{D5}X_{D5}$$

Then, the least-squares method is employed to obtain a multiple regression equation that would minimize the error from a measured value $C_{Di}$ of glucose concentration according to an enzyme electrode method. When the sum of squares of the residual is $R_D$, $R_D$ is expressed by the following equation (2):

$$R_D = \sum_{i=1}^{n} d_{Di}^2 \qquad (2)$$
$$= \sum_{i=1}^{n} (C_{Di} - f(X_{D1i}, X_{D2i}, X_{D3i}, X_{D4i}, X_{D5i}))^2$$
$$= \sum_{i=1}^{n} \{C_{Di} - (a_{D0} + a_{D1}X_{D1i} + a_{D2}X_{D2i} + a_{D3}X_{D3i} + a_{D4}X_{D4i} + a_{D5}X_{D5i})\}^2$$

Because the sum of squares of the residual $R_D$ becomes minimum when partial differentiation of equation (2) with respect to $a_{D0}$, $a_{D2}$, . . . , $a_{D5}$ gives zero. Thus, we have the following equations:

$$\frac{\partial R_D}{\partial a_{D0}} = -2\sum_{i=1}^{n} \{C_{Di} - (a_{D0} + a_{D1}X_{D1i} + a_{D2}X_{D2i} + a_{D3}X_{D3i} + a_{D4}X_{D4i} + a_{D5}X_{D5i})\} \qquad (3)$$
$$= 0$$

$$\frac{\partial R_D}{\partial a_{D1}} = -2\sum_{i=1}^{n} X_{D1i}\{C_{Di} - (a_{D0} + a_{D1}X_{D1i} + a_{D2}X_{D2i} + a_{D3}X_{D3i} + a_{D4}X_{D4i} + a_{D5}X_{D5i})\}$$
$$= 0$$

$$\frac{\partial R_D}{\partial a_{D2}} = -2\sum_{i=1}^{n} X_{D2i}\{C_{Di} - (a_{D0} + a_{D1}X_{D1i} + a_{D2}X_{D2i} + a_{D3}X_{D3i} + a_{D4}X_{D4i} + a_{D5}X_{D5i})\}$$
$$= 0$$

$$\frac{\partial R_D}{\partial a_{D3}} = -2\sum_{i=1}^{n} X_{D3i}\{C_{Di} - (a_{D0} + a_{D1}X_{D1i} + a_{D2}X_{D2i} + a_{D3}X_{D3i} + a_{D4}X_{D4i} + a_{D5}X_{D5i})\}$$
$$= 0$$

$$\frac{\partial R_D}{\partial a_{D4}} = -2\sum_{i=1}^{n} X_{D4i}\{C_{Di} - (a_{D0} + a_{D1}X_{D1i} + a_{D2}X_{D2i} + a_{D3}X_{D3i} + a_{D4}X_{D4i} + a_{D5}X_{D5i})\}$$
$$= 0$$

$$\frac{\partial R_D}{\partial a_{D5}} = -2\sum_{i=1}^{n} X_{D5i}\{C_{Di} - (a_{D0} + a_{D1}X_{D1i} + a_{D2}X_{D2i} + a_{D3}X_{D3i} + a_{D4}X_{D4i} + a_{D5}X_{D5i})\}$$
$$= 0$$

When the mean values of $C_D$ and $X_{D1}$ to $X_{D5}$ are $C_{Dmean}$ and $X_{D1mean}$ to $X_{D5mean}$, respectively, since $X_{Dimean}=0$ (i=1 to 5), equation (4) can be obtained from equation (1) thus:

$$a_0 = C_{mean} - a_1 X_{1mean} - a_2 X_{2mean} - a_3 X_{3mean} - a_4 X_{4mean} - a_5 X_{5mean} \qquad (4)$$
$$= C_{mean}$$

The variation and covariation between the normalized parameters are expressed by equation (5). Covariation between the normalized parameter $X_{Di}$ (i=1 to 5) and C is expressed by equation (6).

$$S_{Dij} = \sum_{k=1}^{n} (X_{Dik} - X_{Dimean})(X_{Djk} - X_{Djmean}) = \sum_{k=1}^{n} X_{Dik} X_{Djk} \qquad (5)$$
$$(i, j = 1, 2, \ldots 5)$$

$$S_{DiC} = \sum_{k=1}^{n} (X_{Dik} - X_{Dimean})(C_{Dk} - C_{Dmean}) = \sum_{k=1}^{n} X_{Dik}(C_{Dk} - C_{Dmean}) \qquad (6)$$
$$(i = 1, 2, \ldots 5)$$

Substituting equations (4), (5), and (6) into equation (3) and rearranging yields simultaneous equations (normalized equations) (7). Solving equations (7) yields $a_{D1}$ to $a_{D5}$.

$$a_1 S_{11} + a_2 S_{12} + a_3 S_{13} + a_4 S_{14} + a_5 S_{15} = S_{1C} \qquad (7)$$
$$a_1 S_{21} + a_2 S_{22} + a_3 S_{23} + a_4 S_{24} + a_5 S_{25} = S_{2C}$$
$$a_1 S_{31} + a_2 S_{32} + a_3 S_{33} + a_4 S_{34} + a_5 S_{35} = S_{3C}$$
$$a_1 S_{41} + a_2 S_{42} + a_3 S_{43} + a_4 S_{44} + a_5 S_{45} = S_{4C}$$
$$a_1 S_{51} + a_2 S_{52} + a_3 S_{53} + a_4 S_{54} + a_5 S_{55} = S_{5C}$$

Constant term $a_{D0}$ is obtained using equation (4). The thus obtained $a_{Di}$ (i=0, 1, 2, 3, 4, 5) is stored in ROM at the time of manufacture of the apparatus. In actual measurement using the apparatus, the normalized parameters $X_{D1}$ to $X_{D5}$ obtained from the measured values are substituted into regression equation (1) to calculate the glucose concentration C.

Similarly, coefficients $a_{Ni}$ (i=1, 2, 3, 4, 5) for the able-bodied persons are determined in advance from measurement data from many diabetic patients and are then stored in ROM as a regression function (8) for able-bodied persons.

$$C = f(X_{N1}, X_{N2}, X_{N3}, X_{N4}, X_{N5})$$
$$= a_{N0} + a_{N1}X_{N1} + a_{N2}X_{N2} + a_{N3}X_{N3} + a_{N4}X_{N4} + a_{N5}X_{N5} \quad (8)$$

Hereafter, an example of the process of calculating the glucose concentration will be described. The coefficients in regression equation (1) are determined based on large data obtained by measuring diabetic patients in advance. The ROM in the microprocessor stores the following formula (9) for the calculation of glucose concentration, in which ROM there is further stored mean values and standard deviations of the parameters $x_1$ to $x_5$:

$$C=205.3+19.8 \times X_{D1}-18.7 \times X_{D2}-24.1 \times X_{D3}-23.0 \times X_{D4}-25.2 \times X_{D5} \quad (9)$$

Similarly, a formula (10) for the calculation of glucose concentrations for able-bodied persons, and average values and standard deviations of parameters $x_1$ to $x_5$ are stored in the ROM.

$$C=95.2+8.7 \times X_{N1}-7.2 \times X_{N2}-8.1 \times X_{N3}-7.8 \times X_{N4}-9.0 \times X_{N5} \quad (10)$$

$X_{D1}$ to $X_{D5}$ are the results of normalization of parameters $x_1$ to $x_5$ with mean value and standard deviation of the diabetic patients. $X_{N1}$ to $X_{N5}$ are the parameters $x_1$ to $x_5$ normalized by the mean value and standard deviation of the able-bodied persons. Assuming the distribution of the parameters is normal, 95% of the normalized parameter takes on values between −2 to +2.

As an example of the measurement values of a diabetic patient, when the values of normalized parameters $X_1$=+0.15, $X_2$=−0.10, $X_3$=−0.22, $X_4$=−0.11, and $X_5$=−0.09 are substituted into equation (9), C=220 mg/dL. As an example of measurement value for an able-bodied person, when the values of normalized parameters $X_{N1}$=−0.05, $X_{N2}$=+0.03, $X_{N3}$=+0.06, $X_{N4}$=−0.10, and $X_{N5}$=+0.12 are substituted into equation (10), C=94 mg/dL.

Hereafter, the details will be described of the measurement using the apparatus in which mean values and standard deviations of $x_1$ to $x_5$ as well as the calculation formula for the glucose concentration for the diabetic patient and the able-bodied person individually are stored.

Figure 9:
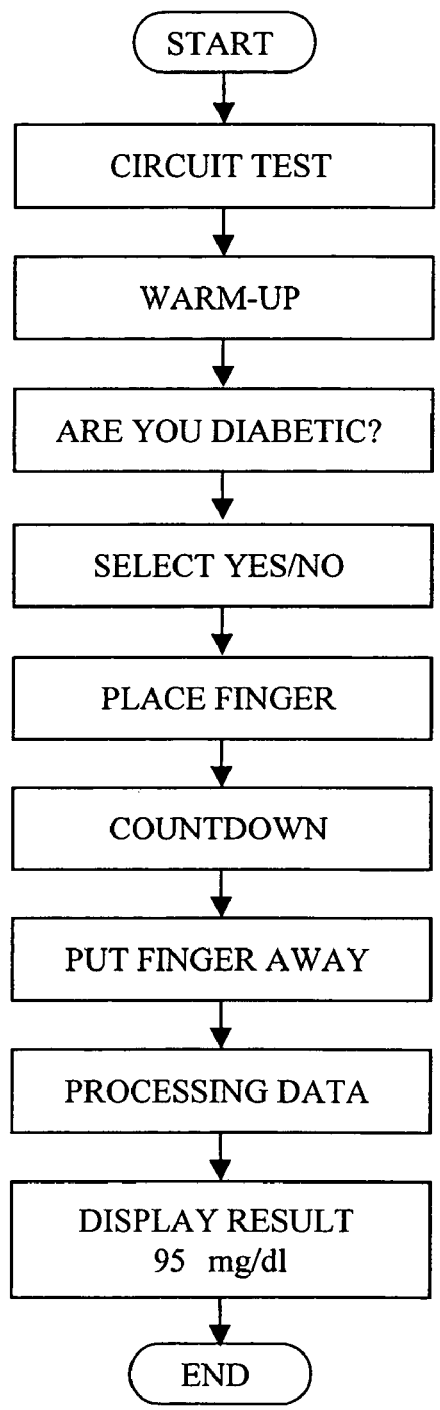
FIG. 9 shows the procedure for operating the apparatus.

FIG. 9 shows the operating procedure of the apparatus, which includes the step of selecting a diabetic patient and an able-bodied person using a selecting portion. As a button on the operating portion, which is a selection inputting means, is pressed to turn the apparatus on, "Warming-up" is displayed on the LCD, and the electronic circuitry in the apparatus is warmed up. Simultaneously, a check program is activated to automatically check the electronic circuitry. As the "Warming-up" comes to an end, a question "Are you diabetic?" appears on the LCD, prompting the subject to enter an input indicating whether or not he is a diabetic patient. The push button 11d is for "Yes" and the push button 11a is for "No." Depending on the content entered here, the software stored in ROM selects necessary functions for determining glucose concentration as well as mean values and standard deviations necessary for the calculation of a normalized parameter as will be described later. The details of the operation flow of the selecting portion will be described later. After the subject has pressed the button for either "Yes" or "No", the LCD displays "Place your finger." As the subject places his finger on the finger rest portion, a countdown is indicated on the LCD. As the subject separates his finger away from the finger rest portion, the LCD displays "Processing data." Afterwards, a blood sugar level is displayed on the LCD. At this point, the displayed blood sugar level is stored in the IC card 43 together with the date and time. As the subject reads the displayed blood sugar level, he presses a button on the operating portion. About one minute later, a message "Place your finger" appears on the LCD, and the apparatus stands by for the subsequent measurement.

Figure 10:
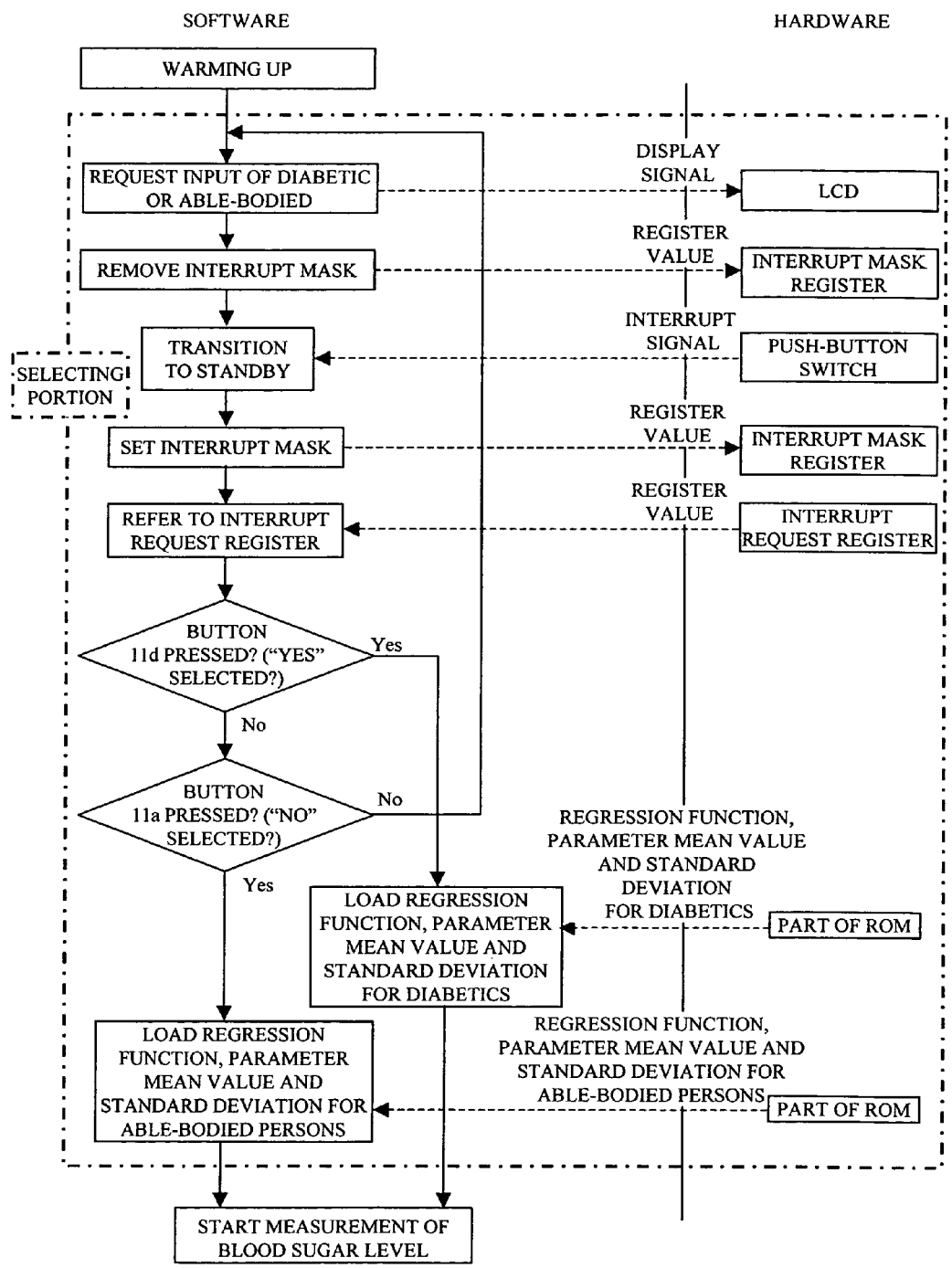
FIG. 10 shows in detail the flow of operation of the selecting portion.

FIG. 10 shows the operation flow of the selecting portion in detail. The selecting portion is the mechanism for selecting a diabetic patient or an able-bodied person, as shown in FIG. 10. After warm-up, an input request message is displayed on the LCD prompting the subject to identify himself as a diabetic patient or not. Specifically, the input request message request an input by assigning the push button 11d to "Yes" and the push button 11a to "No." Thereafter, the software clears the interrupt mask register to zero so that a request for an interrupt processing can be entered by the pressing of a button. Then, the microprocessor is transitioned into a standby mode in order to reduce current consumption. As the subject presses a particular button, an interrupt processing request is issued to the microprocessor, whereupon the microprocessor returns back from the standby mode. Thereafter, the software sets the interrupt processing mask register to 1, thus masking an interrupt processing request via the pressing of a button. The software then reads the interrupt request register to determine which button has been pressed. If the button 11d has been pressed, the subject is a diabetic patient, so that the software loads from ROM a regression function for diabetic patients and mean values and standard deviations of individual parameters for diabetic patients. If the button 11a has been pressed, the subject is an able-bodied person, so that the software loads from ROM a regression function for able-bodied persons and mean values and standard deviations for individual parameters for able-bodied persons. The button 11b or 11c is for the input of any other measurement conditions. These buttons when pressed are invalid and therefore the routine returns to the step of requesting the subject to make an input. Such is the flow of operation in the selecting portion, and a blood sugar measurement is started upon selection of a diabetic patient or an able-bodied person using the selecting portion.

Hereafter, the results of measurement by the conventional enzymatic electrode method and those by an embodiment of the invention will be discussed. In the enzymatic electrode method, a blood sample is reacted with a reagent and the amount of resultant electrons is measured to determine glucose concentration. As an example of the measurement values obtained form a diabetic patient, when the glucose concentration determined by the enzymatic electrode method is 236 mg/dL, substituting the normalized parameters obtained at the same time by measuring method of the invention $XN_1$=−0.05, $XN_2$=+0.03, $XN_3$=+0.06, $XN_4$=−0.10, and $XN_5$=+0.12 into the above equation yields C=94 mg/dl. The results thus indicated that the method according to the invention can provide highly accurate glucose concentration values.

Figure 11:
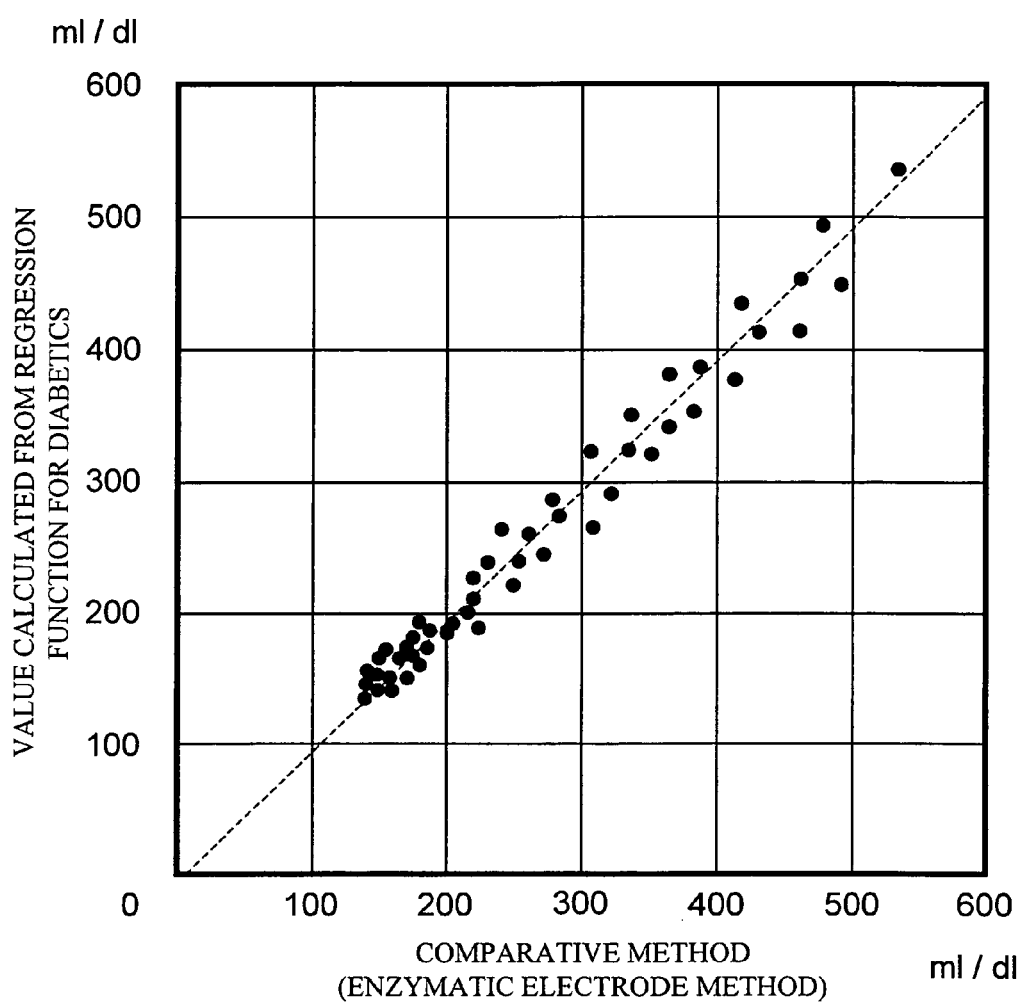
FIG. 11 shows a chart plotting the value calculated by selecting a regression function for diabetic patients and the measurement value obtained by the enzymatic electrode method.
Figure 12:
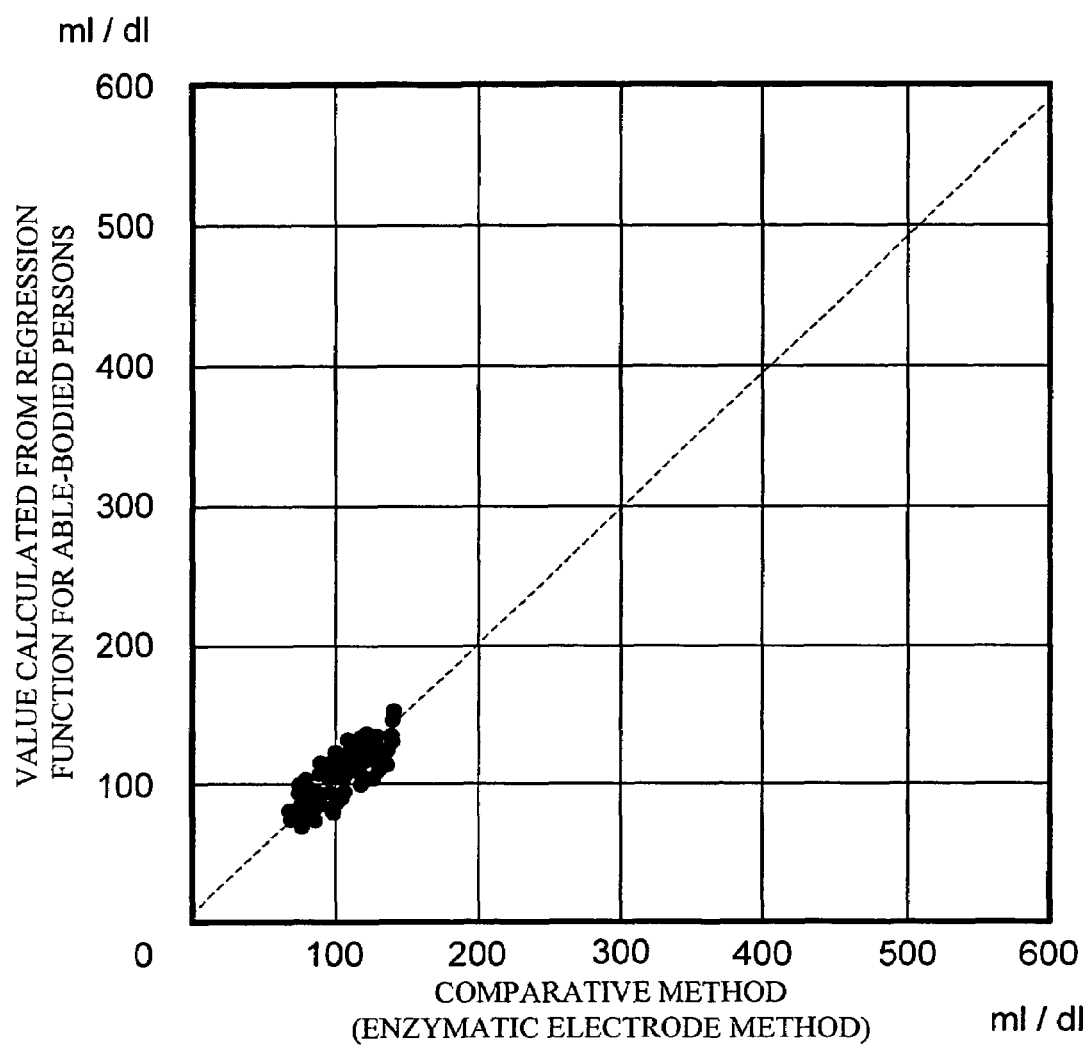
FIG. 12 shows a chart plotting the value calculated by selecting a regression function for able-bodied persons and the measurement value obtained by the enzymatic electrode method.

FIG. 11 shows a chart indicating, on the vertical axis, the glucose concentration measured by the apparatus of the invention in which the regression function for diabetic patients were selected, and, on the horizontal axis, the glucose concentration measured at the same time by the enzymatic electrode method, based on 50 diabetic patients. The correction coefficient is 0.9473. When a line y=Ax+B (y is vertical axis, x is horizontal axis) is fitted for each plot in the chart, using the least-squares method, A=0.992 and B=−6.07. FIG. 12 shows a chart indicating, on the vertical axis, the glucose concentration measured by the present apparatus in which the regression function for able-bodied persons was selected and, on the horizontal axis, the glucose concentration measured simultaneously by the enzymatic electrode method, based on 50 able-bodied persons. The correlation coefficient is 0.9388. When a line y=Cx+D (y is vertical axis, x is horizontal axis) is fitted for each plot in the chart, using the least-squares method, C=0.971 and D=6.84.

Figure 13:
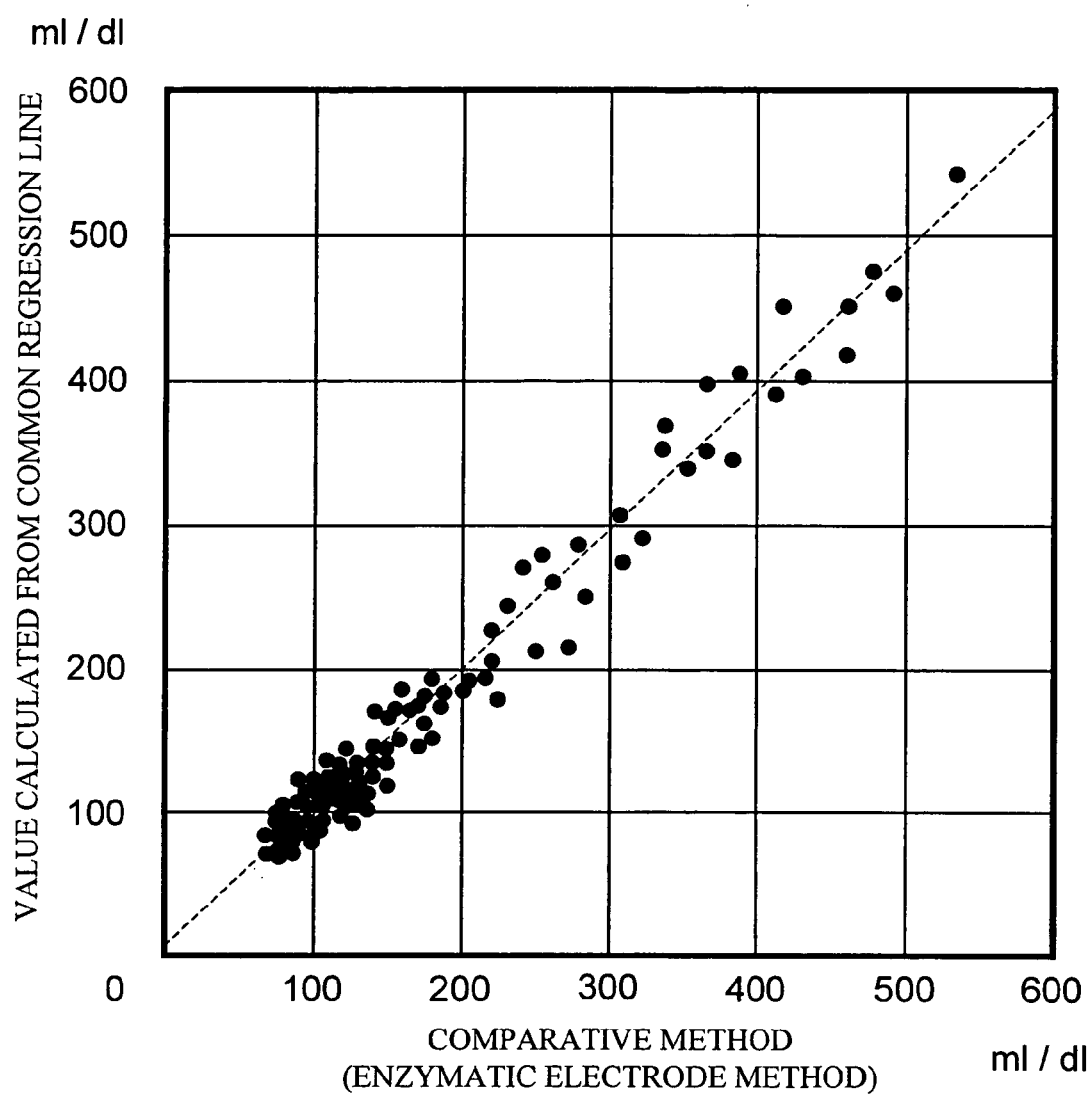
FIG. 13 shows a chart plotting the value calculated by selecting a common regression function for able-bodied persons and diabetic patients and the measurement value obtained by the enzymatic electrode method.

FIG. 13 shows a chart indicating, on the vertical axis, the glucose concentration measured by the present apparatus in which a common regression function obtained from a measurement data group of a subject group consisting of diabetic patients and able-bodied persons, instead of the regression function for either diabetic patients or able-bodied patients. On the horizontal axis of the chart is indicated the glucose concentration measured simultaneously by the enzymatic electrode method. The measurements were conducted on 50 diabetic patients and 50 able-bodied persons, on a total of 100 subjects. The correlation coefficient is 0.9320. When a line y=Ex+F (y is vertical axis, x is horizontal axis) is fitted for each plot in the chart, using the least-squares method, E=0.962 and F=8.15.

The closer the measurement value obtained by the present apparatus is to that by the enzymatic electrode method, the closer the measurement accuracy of the present apparatus is to that of the invasive method. Thus, the chart plotting these values indicates that the closer the correlation coefficient to 1, the higher the measurement accuracy of the present apparatus is. Thus, the results shown in FIGS. 11 to 13 indicate that by conducting measurement by appropriately selecting the regression function for diabetic patients or for able-bodied persons, a higher accuracy of measurement can be achieved than in the case of measurement conducted by using a common regression function obtained from a measurement data group of a subject group consisting of diabetic patients and able-bodied persons.

What is claimed is:

1. A blood sugar level measuring apparatus comprising:
   a measurement portion for obtaining a plurality of measurement values related to a body surface and a measurement environment, including at least a measurement value related to heat measurement;
   a selecting means for selecting an able-bodied person or a diabetic patient; and
   a calculation portion for calculating a blood sugar level based on the plurality of measurement values obtained in the measuring portion and the result of selection by the selecting means.

2. The blood sugar level measuring apparatus according to claim 1, wherein the selecting means comprises a display portion for prompting the selection of either an able-bodied person or a diabetic patient.

3. The blood sugar level measuring apparatus according to claim 1, wherein the selecting means comprises an input operating portion provided for the able-bodied person and diabetic patient individually.

4. The blood sugar level measuring apparatus according to claim 1, further comprising a storage portion in which a plurality of regression functions are stored, wherein the calculation portion reads a regression function corresponding to the result of selection from the storage portion to calculate a blood sugar level.

5. The blood sugar level measuring apparatus according to claim 1, further comprising a storage portion in which a plurality of regression functions and a mean value and a standard deviation of a plurality of parameters corresponding to individual regression functions are stored, wherein the calculation portion reads a regression function corresponding to the result of selection, the mean value of the parameters and the standard deviation from the storage portion and then calculates a blood sugar level.

6. A blood sugar level measuring apparatus comprising:
   an input means for entering an input identifying an able-bodied person or a diabetic patient;
   a heat amount measuring portion for measuring a plurality of temperatures derived from a body surface in order to obtain information used for calculating the amount of transfer of heat by convection and the amount of transfer of heat by radiation, which relate to the dissipation of heat from the body surface;
   an oxygen amount measuring portion for obtaining information relating to the amount of oxygen in blood;
   a storage portion in which a function for able-bodied persons and a function for diabetic patients are individually stored, the functions relating parameters corresponding to the plurality of temperatures and the blood oxygen amount to blood sugar levels;
   a calculation portion for converting a plurality of measurement values inputted from the heat amount measuring portion and the oxygen amount measuring portion into the parameters individually, and applying the parameters to the function stored in the storage portion for the able-bodied persons or for the diabetic patients, depending on the identifying input entered via the input means, in order to calculate a blood sugar level; and
   a display portion for displaying the blood sugar level calculated by the calculation portion.

7. The apparatus according to claim 6, wherein the storage portion stores a regression function for able-bodied persons and another regression function for diabetic patients, and wherein the calculation portion calculates a blood sugar level using the regression function corresponding to the identifying input.

8. The apparatus according to claim 6, wherein the storage portion stores a regression function for able-bodied persons, a regression function for diabetic patients, and a mean value and standard deviation of a plurality of parameters included in each regression function, and wherein the calculation portion calculates a blood sugar level using a regression function corresponding to the identifying input and a mean value and standard deviation associated with that regression function.

9. The blood sugar level measuring apparatus according to claim 6, wherein the oxygen amount measuring portion comprises a blood flow volume measuring portion for obtaining information relating to the volume of blood flow, and an optical measuring portion for obtaining the hemoglobin concentration and hemoglobin oxygen saturation in blood.

10. A blood sugar level measuring method comprising the steps of:
    obtaining a plurality of measurement values relating to a body surface and a measurement environment, including at least a measurement value related to heat measurement;
    obtaining the type identifying an able-bodied person or a diabetic patient; and calculating a blood sugar level using the obtained plurality of measurement values and a regression function for either able-bodied persons or diabetic patients chosen based on the obtained type identifying an able-bodied person or a diabetic patient.

11. The method according to claim 10, wherein the step of calculating blood sugar level comprises:

obtaining a plurality of parameters from the obtained plurality of measurement values;

normalizing the obtained plurality of parameters with a mean value and standard deviation corresponding to the type, i.e. whether an able-bodied person or a diabetic patient; and calculating a blood sugar level by applying the normalized plurality of parameters to the regression function corresponding to the able-bodied person or the diabetic patient.

* * * * *